United States Patent

Wijkamp et al.

[11] Patent Number: 5,167,647
[45] Date of Patent: Dec. 1, 1992

[54] CATHETER WITH A STRAIN RELIEF MEMBER

[75] Inventors: Arnoldus C. J. M. Wijkamp, AW Roden; Robert Antoni, CD Groningen; Hendrik J. Venema, PD Roden, all of Netherlands

[73] Assignee: Cordis Corporation, Miami Lakes, Fla.

[21] Appl. No.: 579,552

[22] Filed: Sep. 10, 1990

[30] Foreign Application Priority Data

Sep. 14, 1989 [NL] Netherlands ............... 8902307

[51] Int. Cl.$^5$ ............................................. A61M 25/00
[52] U.S. Cl. ..................................... 604/281; 604/283
[58] Field of Search .......... 604/95, 103, 159, 164–170, 604/264, 280, 282, 283, 240–243, 281; 128/656–658

[56] References Cited

U.S. PATENT DOCUMENTS

| | | | |
|---|---|---|---|
| 3,312,220 | 4/1967 | Eisenberg | 604/164 |
| 3,469,579 | 10/1969 | Hubert | 604/283 |
| 4,106,506 | 8/1978 | Koehn et al. | 604/164 |
| 4,479,792 | 10/1984 | Lazarus et al. | 128/656 |
| 4,782,819 | 11/1988 | Adair | 604/283 |
| 4,817,613 | 4/1989 | Jaraczewski et al. | 128/658 |
| 4,846,174 | 7/1989 | Willard et al. | 604/96 |
| 4,875,481 | 10/1989 | Higgins | 604/96 |
| 4,969,875 | 11/1990 | Ichikawa | 604/164 |

FOREIGN PATENT DOCUMENTS

| | | |
|---|---|---|
| 0109657 | 5/1984 | European Pat. Off. |
| 0307162 | 3/1989 | European Pat. Off. |
| 81/01519 | 6/1981 | World Int. Prop. O. ......... 604/283 |

Primary Examiner—John D. Yasko
Assistant Examiner—Anthony M. Gutowski
Attorney, Agent, or Firm—Gerstman & Ellis, Ltd.

[57] ABSTRACT

A catheter, such as an angiographic catheter, comprises a flexible, tubular, catheter body which is attached at one end to a strain relief member. A coupling element or hub is carried at the same end of the catheter, with the strain relief member typically extending over a predetermined distance in secured relation with the coupling element. In accordance with this invention, at least a portion of the strain relief member protruding outside of said coupling element has a profiled outer surface to facilitate axial rotation of the catheter with the fingers. The profiled surface may comprise longitudinal ridges, or it may comprise a knurled surface, for example.

12 Claims, 2 Drawing Sheets

CATHETER WITH A STRAIN RELIEF MEMBER

BACKGROUND OF THE INVENTION

The invention relates to a catheter, such as a catheter for angiographic tests, comprising a flexible tubular basic body which is attached at one side with a strain relief extending over a determined distance into a coupling element.

Such a catheter is generally known. For example, in angiographic testing a catheter is guided through a vein until the outlet end thereof is carried into or close to the heart. A known coupling element remains outside the body of the patient and serves for coupling the catheter with, for example, a syringe for the admittance of contrast medium.

In order to minimize the discomfort for the patient attempts are being made to manufacture catheters with a smaller diameter. It has been found in practice however that the manageability of thinner catheters becomes increasingly more difficult. The person inserting the catheter into the patient has to be able to manipulate it properly. In particular, the catheter must be rotated about its lengthwise axis when insertion takes place, which the person performing the insertion accomplishes by rolling the catheter between his or her fingers. In the case of a catheter of small diameter the grip is insufficient to enable it to be rotated in a reliable manner.

The invention now has for its object to provide a catheter of the type described above which can be embodied with a small diameter and which can nevertheless be manipulated properly and reliably by the user.

SUMMARY OF THE INVENTION

This object is achieved with a catheter according to the invention in that the strain relief member for the tubular body has a profiled outer surface, such as longitudinal ribs. As a result the user can gain a more than sufficient purchase on the strain relief member for rolling the catheter between the fingers, so that a catheter can still be manipulated properly when it is of small diameter. In practice there is no objection during insertion to holding the catheter for rotation at the strain relief member instead of at a random part of the basic body.

The strain relief member can be extruded in substantial lengths in the form of a tube, whereby the opening of the extrusion die defining the outer tube surface is provided with a profiling, so that the extruded strain relief member is provided with lengthwise ridges, for example, on its outer surface. The required length for each strain relief member may be cut from the greater extruded length and pushed over the end of the tubular body of the catheter. The coupling element or hub may be subsequently glued into position on the end. The length of the strain relief member is of course chosen such that the finished catheter has enough free strain relief member to provide a good gripping surface.

According to a further development of the invention, instead of extruding the strain relief member, the end of the tubular body of the catheter can be arranged in an injection mould, and the strain relief member can be formed and applied to the body by injection molding. The coupling element or hub may subsequently be glued in place onto the end, or it may also be molded in place. Through the injection molding of the strain relief member, the outer surface thereof can have a profiled pattern, for example, random projections or a serrated form.

In another method a preformed coupling element can, with the tubular body of the catheter, be arranged in the mould, and the strain relief member can be injection molded onto both elements, whereby the strain relief member simultaneously connects the basic body to the coupling element.

Another option for the manufacture of a catheter according to the invention is to mold and connect the strain relief member and the coupling element simultaneously in an injection mould, whereby for the two components different materials, and in particular different plastics, are used. Injection molding with two different materials is a per se known art.

DESCRIPTION OF THE DRAWINGS

The invention will be further elucidated in the following description with referenced to several embodiments shown in the figures

DESCRIPTION OF THE SPECIFIC EMBODIMENTS

Figure 1:
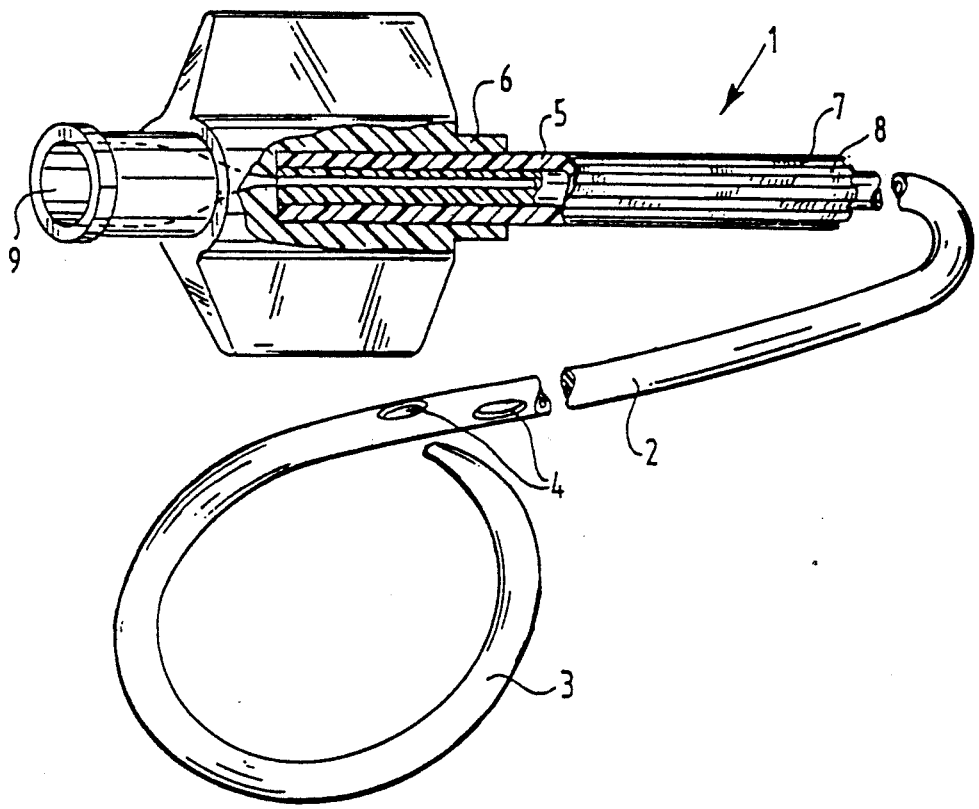
FIG. 1 shows a partly broken away view of a catheter according to the invention.

The catheter 1 shown in FIG. 1 is intended for angiographic tests. This catheter 1 comprises a basic tubular body 2 which is manufactured in the usual manner from a plastic such a polyurethane with an internal reinforcing layer of thinly-woven steel thread.

The outlet end part 3 of the catheter is heat formed into a curl-shape and is provided with a number of outlet openings 4, while the outermost end is moreover open. The catheter 1 shown is therefore of the so-called pigtail type.

At the other end of the catheter 1 a coupling element or hub 6 is arranged. This coupling element is provided with a female Luer connection 9 so that for example a syringe can be attached to the catheter. A strain relief tube 5 is pushed over the proximal end portion of the tubular body 2, while strain relief tube 5 is secured in an aperture in the coupling element 6. Strain relief member 5 serves to reinforce the catheter at that location. The end portion of the tubular body 2 is inserted, together with the relief strain member 5 pushed thereon, into the recess formed for the purpose in the coupling element 6, and glued therein.

According to the invention, at least the portion of the strain relief member 5 protruding outside the coupling element 6 is provided with a profiled outer surface. In the embodiment of FIG. 1 the profiling of the outer surface is achieved by providing it with longitudinal ridges 8 which alternate with longitudinal grooves 7. The person inserting the catheter into the patient can, as a result, acquire a proper grip on the catheter when wishing to rotate it around its lengthwise axis by grasping and rolling between index finger and thumb that portion of the strain relief member 5 protruding outside the coupling element 6 and provided with the profiled outer surface.

The strain relief member 5 can be manufactured by extruding it in substantial lengths. For this purpose the extrusion aperture of an extrusion die defining the outer surface of the strain relief member has in a per se known manner a profiling, such that the grooves 7 and ridges 8 are formed during extrusion. Pieces are cut from the length of extruded material to use as the strain relief member 5, being pushed during assembly onto body 2 and glued into coupling element 6 together with body 2.

The strain relief member 5 can also be formed in other ways as may be desired.

Figure 2:
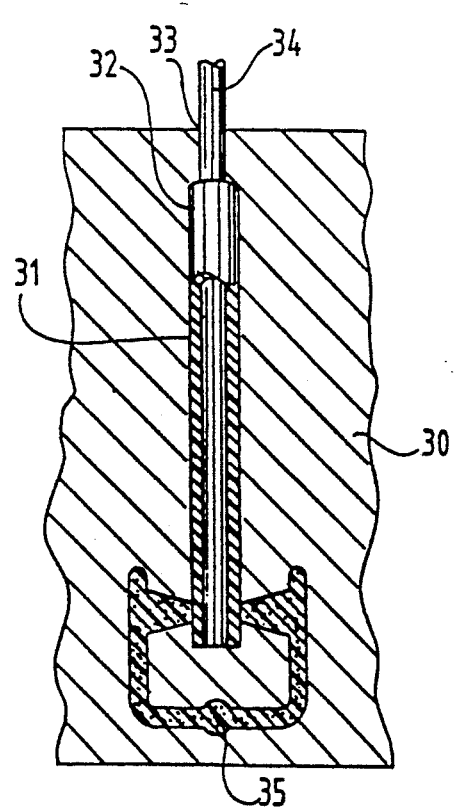
FIG. 2 shows schematically a phase in the manufacture of a catheter according to the invention.

As shown in FIG. 2, a tubular strain relief 32 is formed in a schematically depicted injection mould 10. Injection molding is a per se known art, and a schematic representation will therefore suffice.

Mould 30 has a mould cavity 31, the surface of which is profiled, for instance ridged or knurled, and which defines the outer surface of tubular strain relief 32.

The mould is further provided with an opening 33 through which the proximal or rear end of the tubular body 34 of a catheter is inserted in a molten state into the mould in the usual manner via material feed channels 35. The strain relief 32 is formed around the inserted end of the basic body 34. After cooling, the assembly can be removed from the mould 30 and can be further finished, among other things by adhering a coupling element thereto.

Figure 3:
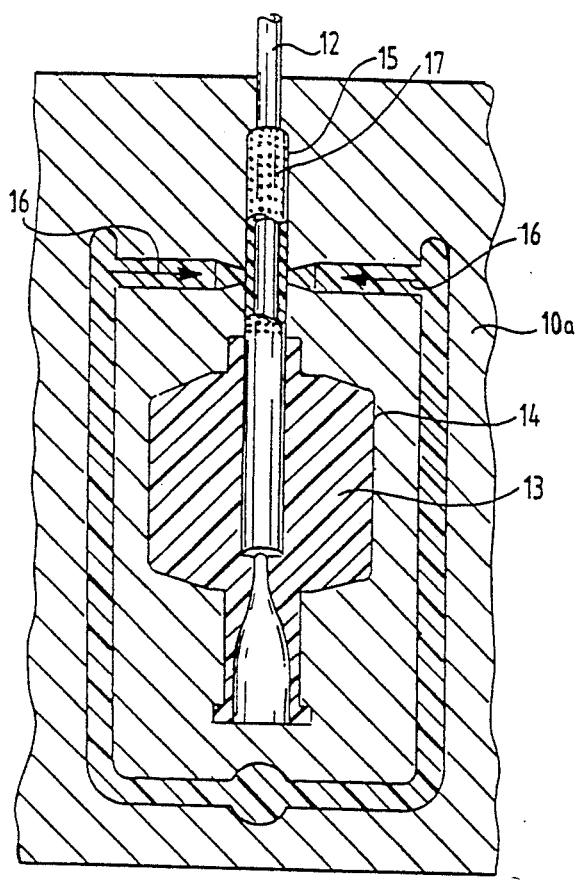
FIG. 3 shows a view of another embodiment corresponding with FIG. 2.

Another production method is shown schematically in FIG. 3. Here it can be seen that a cavity 14 is formed in a mould 10a in which a preformed coupling element or hub 13 can be arranged in closefitting manner. The mould 10 is moreover also provided here with recesses for the passage of a tubular catheter body 12, an end of which is inserted into the coupling element 13. When the mould is closed, and the coupling element with the inserted basic body 12 is arranged therein, a mould cavity 15 is leftover which defines the strain relief member. By feeding plastic in liquid form under pressure into the cavity 15 in the known manner, indicated schematically with arrow 16, the cavity 15 is filled, and the strain relief is thus formed. The wall of the cavity 15 defines the outer surface of the strain relief member and can be provided with any suitable profiling 17 so that the outer surface of the strain relief can likewise have profiling in order to acquire the required grip.

Figure 4:
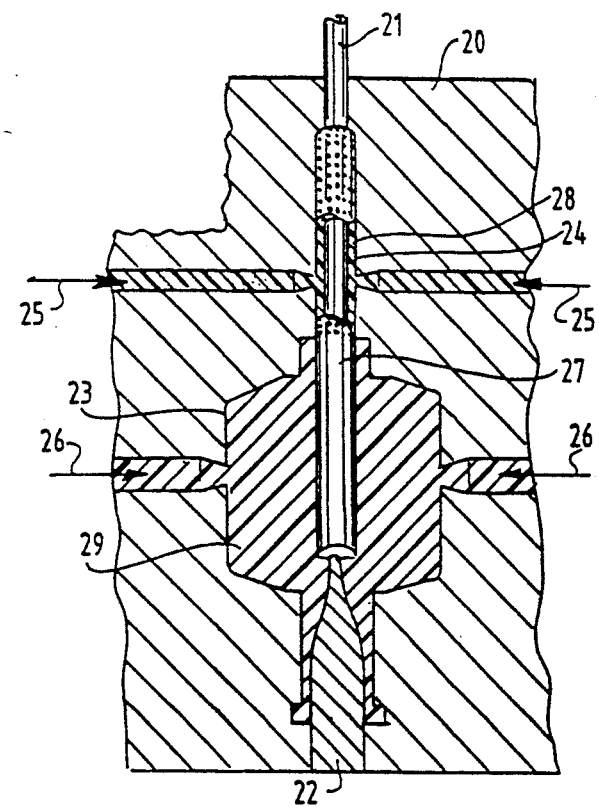
FIG. 4 shows a view of yet another embodiment corresponding with FIGS. 2 and 3.

According to a further intended production method for the catheter according to the invention, use is made in FIG. 4 of a per se known injection molding method, whereby two different materials can be injected simultaneously. The mould 20, shown schematically in FIG. 4, comprises both a mould cavity 23 for a coupling element 29 and a mold cavity 14 for a strain relief member. In the mould 20 a recess is arranged for receiving a catheter body 21. This body 21 is pushed with its end onto the mandrel 22, protruding into the mold cavity 23 in order to ensure an open connection with the lumen of the catheter body 21.

After the catheter body 21 has been thus arranged in the mould 20 and the mold has been closed, different plastics can be injected in liquid form into the formed cavities 23 and 24 if desired as designated schematically with the respective arrows 25 and 26. After cooling, coupling element 29 and strain relief member 28 are thus formed. As before, strain relief member 28 may have a profiled, molded outer surface.

When forming and connecting of the strain relief member, and optionally the coupling element, takes place by injection molding, as described with reference to FIGS. 2 and 4, the material of the strain relief and optionally the coupling element fuse with that of the body of the catheter so that this method of manufacture has the added advantage that a separate gluing process may be unnecessary.

The above has been offered for illustrative purposes only and is not to be considered as limiting the invention, which is as defined in the claims below.

That which is claimed is:

1. A catheter, such as a catheter for angiographic tests, comprising a flexible, tubular catheter body which is attached at one end within a strain relief member extending over a predetermined distance in secured relation with a coupling element, characterized in that at least the portion of said strain relief member protruding outside of said coupling element has a generally cylindrical but profiled outer surface to facilitate axial rotation of the catheter with the fingers, said strain relief member defining a portion that is molded in place about said catheter body and extending into said coupling element in telescoping relation therewith, said portion being permanently secured within said coupling element, said catheter defining, at its end opposed to said coupling element, a pigtail-type curled tip.

2. The catheter of claim 1 characterized in that the strain relief member is provided with ridges extending in lengthwise direction.

3. The catheter of claim 1, characterized in that the strain relief member is provided with a knurled surface.

4. The catheter of claim 1 in which said coupling element and strain relief member are simultaneously molded in place on said catheter body.

5. The catheter of claim 1 in which said strain relief member is made from extruded plastic tubing.

6. In an angiographic catheter which comprises a flexible, tubular catheter body attached at its proximal end to a tubular strain relief member, with the tubular catheter body fitting within the lumen of said tubular strain relief member, said strain relief member extending over a predetermined distance in secured relation with a coupling element, the improvement comprising, in combination, said strain relief member defining a portion projecting outwardly from said coupling element along said catheter body, said portion having a generally cylindrical exterior surface which carries outwardly extending projections to facilitate axial rotation of the catheter with the fingers, said strain relief member defining a portion that is molded in place about said catheter body and extending into said coupling element in telescoping relation therewith, said portion being permanently secured within said coupling element, said catheter defining, at its end opposed to said coupling element, a pigtail-type curled tip.

7. A catheter of claim 6 in which said strain relief member carries projections which define longitudinal ridges.

8. The catheter of claim 7 in which said coupling element and strain relief member are simultaneously molded in place on said catheter body.

9. The catheter of claim 7 in which said strain relief member is made from extruded plastic tubing.

10. The catheter of claim 1 in which said strain relief member is of less diameter than said coupling element.

11. The catheter of claim 6 in which said strain relief member is of less diameter than said coupling element.

12. The catheter of claim 11 in which said strain relief member carries projections which define longitudinal ridges.

* * * * *